United States Patent [19]

Raynor et al.

[11] Patent Number: 5,068,408

[45] Date of Patent: Nov. 26, 1991

[54] HYPOCHLOROUS ACID AS A REAGENT FOR THE OXIDATION OF ORGANIC COMPOUNDS IN TWO PHASE SYSTEMS

[75] Inventors: Robert J. Raynor, North Branford, Conn.; Budd L. Duncan, Athens, Tenn.

[73] Assignee: Olin Corporation, Cheshire, Conn.

[21] Appl. No.: 473,084

[22] Filed: Jan. 31, 1990

[51] Int. Cl.$^5$ ............... C07C 51/29; C07C 29/48; C07C 37/60; C07C 45/27; C07C 253/00

[52] U.S. Cl. ............... 562/419; 558/308; 558/313; 560/338; 562/531; 562/538; 562/859; 564/271; 564/278; 568/26; 568/27; 568/28; 568/322; 568/426; 568/485; 568/910

[58] Field of Search ............... 560/338; 562/419, 531, 562/538, 859; 558/308, 313; 568/426, 485, 322, 910, 27, 28, 26; 564/271, 278

[56] References Cited

U.S. PATENT DOCUMENTS

| | | | |
|---|---|---|---|
| 3,996,259 | 12/1976 | Lee et al. ............... | 562/419 X |
| 4,079,075 | 3/1978 | Lee et al. ............... | 562/419 X |
| 4,683,342 | 7/1987 | Pittet et al. ............... | 568/425 X |
| 4,814,494 | 3/1989 | Shimizu et al. ............... | 562/419 |

OTHER PUBLICATIONS

Kirk-Othmer Encyclopedia of Chemical Technology, vol. 5, Third Edition, pp. 62–68, John Wiley & Sons, Inc., New York, (1979).

Lee et al., Tetrahedron Letters, vol. 20, pp. 1641–1644, (1976).

*Primary Examiner*—Jose G. Dees
*Assistant Examiner*—Vera C. Clarke
*Attorney, Agent, or Firm*—F. A. Iskander; Donald M. Papuga

[57] ABSTRACT

A process for oxidizing an organic compound selected from an aliphatic, aromatic, aliphatic/aromatic, cycloaliphatic and heterocyclic alcohol, thiol, sulfide, aldehyde, amine, amide, ketone, acid, ether, ester, and organic compounds containing an activated carbon-carbon double bond, which process comprises contacting said organic compound dissolved in an organic solvent with a hypochlorous acid solution.

21 Claims, No Drawings

HYPOCHLOROUS ACID AS A REAGENT FOR THE OXIDATION OF ORGANIC COMPOUNDS IN TWO PHASE SYSTEMS

This invention is directed to the use of hypochlorous acid to cause the facile oxidation of organic compounds, which are suitable to oxidation, in two phase reaction systems (aqueous/organic) without the use of phase-transfer catalysts usually required to initiate and sustain this type of reaction.

Oxidation of organic compounds is a well-known method to produce a wide variety of organic compounds from aliphatic, aromatic, aliphatic/aromatic, cycloaliphatic and heterocyclic alcohols, thiols, sulfides, aldehydes, amines, amides, ketones, acids, ethers, esters, and compounds containing an activated carbon-carbon double bond.

Numerous processes and reagents have been used to oxidize these organic compounds. Oxidations have often been carried out in polar aprotic solvents. However, due to the expense of the aprotic solvents, recycling of solvent, long reaction times, high reaction temperatures, etc., other methods were developed. One of these methods was the oxidation of organic compounds in a two phase media (aqueous/organic) which allowed the use of inexpensive oxidants, such as hypohalites.

For example, U.S. Pat. Nos. 3,996,259 and 4,079,075 describe the oxidation of organic compounds such as amines, amides, primary and secondary alcohols, and alkanols using a hypohalite and a phase transfer catalyst. The reaction is carried out in a two phase system, a water immiscible, liquid organic phase containing an organic compound oxidizable by hypohalite, and an aqueous phase containing the hypohalite ion. The hypohalite ion is produced from an alkali metal hypohalite. A phase transfer catalyst is required to carry the hypohalite ion from the water phase into the organic phase, thus permitting its reaction (oxidation) with the organic compound contained in that phase.

Lee, et al., Tetrahedron Letters, 20 May 1976, pp 1641-1644, describe oxidation of alcohols and amines by aqueous hypochlorite using a phase transfer catalyst which is a lipophilic quaternary ammonium salt for the transfer of anionic species from aqueous to organic media.

The use of the phase transfer catalyst in the oxidation of organic compounds in two phase systems had several advantages: no need for expensive aprotic solvents; simpler workup; shorter reaction time; and lower reaction temperatures.

However, in all such oxidation processes performed in the two phase system, a phase transfer catalyst was required. Without the catalyst, such reactions were often slow or did not occur. In this regard, E. V. Dehmlow, in a section titled Catalysis, Kirk-Othmer, Encyclopedia of Chemical Technology, 3rd Edition, Volume 5, John Wiley & Sons, Inc., 1979, discusses phase transfer catalysts on pages 62 to 68.

On page 62, this publication states the following:
"Phase-transfer catalysis (PTC) is a technique by which reactions between substances located in different phases are brought about or accelerated. Typically, one or more of the reactants are organic liquids or solids dissolved in a nonpolar organic solvent, and the coreactants are salts or alkali metal hydroxides in aqueous solution. Without a catalyst, such reactions are often slow or do not occur at all; the phase-transfer catalyst, however, makes such conversions fast and efficient."

On page 68, oxidation of alcohols to aldehydes and ketones, and oxidation of an amine to a nitrile is illustrated using sodium hypochlorite under PTC conditions.

In this invention, it has been found that the use of hypochlorous acid causes the facile oxidation of organic compounds in two phase (aqueous/organic) systems without the use of a phase transfer catalyst. Further, the instant process does not require the use of an alkali metal hypohalite but rather, utilizes a hypochlorous acid solution.

The elimination of the use of the phase transfer catalyst has several advantages, i.e., it eliminates catalyst cost and also separation and isolation procedures associated with the catalyst.

This invention is directed to the oxidation of organic compounds such as aliphatic, aromatic, aliphatic/aromatic, cycloaliphatic and heterocyclic alcohols, thiols, sulfides, aldehydes, amines, amides, ketones, acids, ethers, esters, and compounds containing an activated carbon-carbon double bond by the use of hypochlorous acid. In a preferred embodiment of this invention, a highly concentrated form of hypochlorous acid is used, wherein the hypochlorous acid is present in amounts of greater than about 25% by weight.

A wide variety of organic compounds may be oxidized by the process of this invention. Illustrative of these compounds are aliphatic, aromatic, cycloaliphatic, and heterocyclic alcohols, thiols, sulfides, aldehydes, amines, amides, ketones, acids, ethers, esters, and organic compounds containing an activated carbon-carbon double bond. Oxidation of these compounds is well known in the art. Typical reactions include oxidation of alcohols to aldehydes; oxidation of aldehydes to acids; oxidation of amines to imines or nitriles; oxidation of enones to epoxides; oxidation of thiols to sulfonyl chlorides; oxidation of sulfides to sulfones and sulfoxides; oxidation of amides to isocyanates; and the like.

The hypochlorous acid used in the instant process may be characterized as a solution containing from about 5 to about 65, preferably from about 25 to about 60, and most preferably from about 30 to about 50% by weight of hypochlorous acid (HOCl).

The concentrated hypochlorous acid solution can contain greater than about 25% by weight of HOCl. This solution may be produced from a gaseous mixture comprised of chlorine monoxide, hypochlorous acid vapor, chlorine, and water vapor, which process comprises condensing the gaseous mixture at a temperature in the range of from about $-5°$ C. to about $+10°$ C.

In more detail, a process for producing the concentrated hypochlorous acid solution comprises reacting an aqueous alkali metal hydroxide, such as sodium hydroxide, potassium hydroxide, or lithium hydroxide in droplet form with chlorine gas. The reaction is conducted at temperatures sufficiently high enough to vaporize hypochlorous acid as it is produced and separate it from solid particles of alkali metal chloride which are also formed in the reaction. As gaseous mixtures having high concentrations of hypochlorous acid and chlorine monoxide are desired, highly concentrated aqueous solutions of the alkali metal hydroxide are used. Suitable concentrations include those in the range of from about 40 to about 80%, and preferably from about 45 to about 60% by weight of alkali metal hydroxide. A stoichiometric excess of chlorine above that required to form hypochlorous acid with all of the alkali metal hydroxide is used, for example from about 1 to about 20, and preferably from about 5 to about 10 times the stoichiometric proportion of chlorine is employed. Solid particles of alkali metal chloride are also produced during the reaction which have a wide range of particles sizes.

The gaseous mixture comprised of hypochlorous acid vapor, chlorine monoxide, chlorine, and water vapor used in the process contains high concentrations of HOCl and Cl$_2$O. The chlorine monoxide is formed by the conversion of HOCl vapors during the vaporization process according to the equation:

$$2HOCl \rightleftharpoons Cl_2O + H_2O$$

The gaseous mixture also contains fine particles of the alkali metal chloride which are entrained. The solid particles may be removed by any suitable separation means, for example, by passing the gaseous mixture through a gas filter medium or through a solid separator such as a cyclone.

The gaseous mixture, now free of solids, is fed to a condenser. The condenser is operated at temperatures which produce concentrated aqueous solutions of hypochlorous acid without condensing undesirable amounts of chlorine or liquid chlorine monoxide. Suitable temperatures for operating the condensation process include those in the range of from about $-5°$ C. to about $+20°$ C.

The hypochlorous acid solution has a concentration greater than about 25% by weight of HOCl.

The uncondensed gaseous mixture recovered from the condenser is substantially anhydrous as the water vapor originally present was condensed to form the aqueous hypochlorous acid solution. While the hypochlorous acid concentration is significantly reduced, the chlorine gas concentration is substantially the same as that in the original gaseous mixture fed to the condenser.

The concentrated hypochlorous acid solution prepared as described above is highly pure. The concentrated hypochlorous acid solution is essentially free of ionic impurities such as alkali metal, chloride, and chlorate ions. Concentrations of the chloride ion are less than about 50 parts per million; the alkali metal ion concentration is less than about 50 parts per million; and the chlorate ion concentration is no more than about 100 parts per million. The hypochlorous acid solution consists essentially of hypochlorous acid and water.

A process for producing hypochlorous acid is described, for example, in U.S. Pat. No. 4,146,578, incorporated in its entirety herein by reference.

The oxidation process of this invention may be conducted over a wide range of reaction conditions depending upon the particular organic compound to be oxidized. Typical temperature ranges include those from about $-20°$ C. to about 100° C., preferably from about 0° C. to about 35° C.

The oxidation of the organic compound is carried out in a two-phase system, i.e., aqueous and organic. The hypochlorous acid solution constitutes the aqueous phase.

The organic compound dissolved in a solvent constitutes the organic phase. The solvent can be characterized as any solvent capable of dissolving the organic compound to be oxidized and inert to reaction with the hypochlorous acid solution. Typical solvents include methylene chloride, chloroform, ethyl acetate, and the like. The amount of solvent used is generally equal to or greater than the volume of the hypochlorous acid solution.

The molar ratio of the hypochlorous acid in the aqueous phase to the organic compound in the organic phase is generally from 0.5 to 1 to about 10 to 1.

The reaction may be carried out by dissolving the organic compound to be oxidized in the appropriate solvent and adding thereto the hypochlorous acid solution.

EXAMPLES

The following examples illustrate the process of this invention and are presented without the intention of being limited thereby.

Preparation of Hypochlorous Acid Solution

The following represents typical preparation of a concentrated hypochlorous acid solution useful in this invention:

A gaseous mixture containing an average concentration of 180.7 parts by weight of chlorine monoxide, 384.5 parts by weight of Cl$_2$, and 60.3 parts by weight of water vapor was continuously passed through a cyclone separator to remove any entrained solid particles of alkali metal chloride. The solid-free gaseous mixture at a temperature of 85°–90° C. was passed through a vertical shell and tube heat exchanger maintained at a temperature of about 0° C. and a pressure of about 3–4 torr gauge to condense a portion of the chlorine monoxide and substantially all of the water vapor to produce an aqueous hypochlorous acid solution containing 45 to 50% by weight of HOCl. The hypochlorous acid solution had a pH of about 1 and the dissolved chlorine concentration was determined to be about 1% by weight. An uncondensed gas mixture containing an average of 141.9 parts by weight of Cl$_2$O, 384.1 parts by weight of Cl$_2$ and 0.5 parts by weight of water was continuously removed from the condenser. The uncondensed gas mixture was passed through a heat exchanger to raise the temperature to about 100° C. and recycled to a generator used to produce the gaseous mixture of chlorine monoxide.

EXAMPLE 1

A solution of 10.6 g (0.1 m) benzaldehyde in 50 ml methylene chloride contained in a 100 ml flask, and stirred by means of a magnetic stirrer, was cooled to 5° C. by means of an ice bath. To this stirred solution was added over a 10 minute period and by means of a dropping funnel 44 g of a 30% aqueous solution of hypochlorous acid (0.25 m HOCl). The mixture was rapidly stirred and cooled for an additional 15 minutes at which time a sample of the methylene chloride phase was withdrawn and analyzed by gas chromatography No benzaldehyde remained, and the reaction products were found to be 31% benzoyl chloride and 69% benzoic acid.

EXAMPLE 2

A solution of 5.4 g (0.05 m) benzyl alcohol in 25 ml methylene chloride contained in a 100 ml flask and stirred by means of a magnetic stirrer was cooled to 5° C. by means of an ice bath. To this stirred solution was added over an 8 minute period 22 g of a 30% aqueous solution of hypochlorous acid (0.125 m). After completion of the addition, the temperature of the reaction mixture was 30° C. The mixture was allowed to stir with cooling for an additional 20 minutes at which time the cooling bath was removed and the contents allowed to warm slowly to 25° C. over a 30 minute period. The methylene chloride phase was then analyzed by gas chromatography and found to contain 14.1% unreacted benzyl alcohol, 21.3% benzoyl chloride, and 62% benzoic acid. Stirring for an additional 70 minutes produced a reaction product containing 78% benzoic acid.

COMPARATIVE EXAMPLE

This example illustrates that sodium hypochlorite cannot oxidize an organic compound in a two-phase system without the use of a phase transfer catalyst.

A solution of a 5.4 g (0.05 m) benzyl alcohol in 50 ml of methylene contained in a 300 ml flask was stirred by means of a magnetic stirrer and cooled by means of an ice bath to 5° C. A 5% aqueous solution of sodium hypochlorite in the amount of 186 g (0.125 m) was added from a dropping funnel to the stirred and cooled methylene chloride solution over an 8 minute period. No increase in temperature was observed, and the cooling ice bath was removed. The reaction mixture was then allowed to warm slowly to 25° C. over a 40 minute period. At this time, the methylene chloride phase was analyzed by gas chromatography, and it contained only unreacted benzyl alcohol. Stirring was resumed and 1.0 g of tetrabutyl ammonium hydrogen sulfate was added to the reaction mixture. An immediate increase in the temperature of the mixture to 35° C. was observed, and the ice cooling bath was used to control the reaction temperature. After an additional 40 minutes, the methylene chloride phase was analyzed by gas chromatography and found to contain no benzyl alcohol, 93% benzaldehyde and 5% benzoic acid. The cooling bath was removed and the flask and its stirred contents were allowed to warm slowly to 25° C. After an additional 5½ hours of stirring at 25° C., chromatographic analysis of the methylene chloride phase showed it contained 55% benzaldehyde and 41% benzoic acid.

What is claimed is:

1. A process for oxidizing an organic compound selected from an aliphatic, aromatic, aliphatic/aromatic, cycloaliphatic, and heterocyclic alcohol, thiol, sulfide, aldehyde, amine, amide, ketone, acid, ether, ester, and organic compounds containing an activated carbon-carbon. double bond, which process comprises contacting said organic compound dissolved in an inert organic solvent with a hypochlorous acid solution.

2. A process as defined in claim 1 wherein the hypochlorous acid solution contains from about 5 to about 65% by weight of hypochlorous acid.

3. A process as defined in claim 1 wherein the hypochlorous acid solution contains from about 25 to about 60% by weight of hypochlorous acid.

4. A process as defined in claim 1 wherein the hypochlorous acid solution contains from about 30 to about 50% by weight of hypochlorous acid.

5. A process as defined in claim 1 wherein the organic compound is an aldehyde.

6. A process as defined in claim 1 wherein the organic compound is an alcohol.

7. A process as defined in claim 1 wherein the oxidation is carried out at a temperature of from about −20° C. to about 100° C.

8. A process for oxidizing an aliphatic, aromatic, aliphatic/aromatic, cycloaliphatic and heterocyclic aldehyde, which process comprises contacting said aldehyde dissolved in an inert organic solvent with a hypochlorous acid solution.

9. A process as defined in claim 8 wherein the aldehyde is an aromatic aldehyde.

10. A process as defined in claim 9 wherein the aldehyde is benzaldehyde.

11. A process as defined in claim 8 wherein the hypochlorous acid solution contains from about 25 to about 60% by weight of hypochlorous acid.

12. A process as defined in claim 8 wherein the hypochlorous acid solution contains from about 30 to about 50% by weight of hypochlorous acid.

13. A process for oxidizing an aliphatic, aromatic, aliphatic/aromatic, cycloaliphatic and heterocyclic alcohol, which process comprises contacting said alcohol dissolved in an inert organic solvent with a hypochlorous acid solution.

14. A process as defined in claim 13 wherein the alcohol is an aromatic alcohol.

15. A process as defined in claim 13 wherein the alcohol is benzylalcohol.

16. A process as defined in claim 13 wherein the hypochlorous acid solution contains from about 25 to about 60% by weight of hypochlorous acid.

17. A process as defined in claim 13 wherein the hypochlorous acid solution contains from about 30 to about 50% by weight of hypochlorous acid.

18. A process for oxidizing an organic compound which comprises the following steps:
   (I) forming a hypochlorous acid solution from a gaseous mixture comprised of chlorine monoxide, hypochlorous acid vapor, chlorine, and water vapor comprising condensing the gaseous mixture at a temperature in the range of from about −5° C. to about +10° C., and
   (II) contacting said hypochlorous acid solution with an organic compound dissolved in an inert organic solvent, said organic compound selected from an aliphatic, aromatic, aliphatic/aromatic, cycloaliphatic, and heterocyclic alcohol, thiol, sulfide, aldehyde, amine, amide, ketone, acid, ether, ester, and organic compounds containing an activated carbon-carbon double bond.

19. A process as defined in claim 18 wherein the hypochlorous acid solution contains from about 25 to about 60% by weight of hypochlorous acid.

20. A process as defined in claim 18 wherein the hypochlorous acid solution contains from about 30 to about 50% by weight of hypochlorous acid.

21. A process as defined in claim 18 wherein step (II) is carried out at a temperature of from about −20° C. to about 100° C.

* * * * *